United States Patent
Adam et al.

(10) Patent No.: US 9,512,150 B2
(45) Date of Patent: Dec. 6, 2016

(54) THERMAL CONDUCTIVE COMPOSITIONS AND METHODS FOR THEIR PREPARATION AND USE

(71) Applicant: EMPIRE TECHNOLOGY DEVELOPMENT LLC, Wilmington, DE (US)

(72) Inventors: Georgius Abidal Adam, Edensor Park (AU); Mordehai Margalit, Zichron Ya'akov (IL); Bradley Kirk Roberts, Seattle, WA (US); Feng Wan, Issaquah, WA (US)

(73) Assignee: Empire Technology Development LLC, Wilmington, DE (US)

( * ) Notice: Subject to any disclaimer, the term of this patent is extended or adjusted under 35 U.S.C. 154(b) by 108 days.

(21) Appl. No.: 14/448,938

(22) Filed: Jul. 31, 2014

(65) Prior Publication Data
US 2016/0031914 A1    Feb. 4, 2016

(51) Int. Cl.
| | |
|---|---|
| *C07D 257/02* | (2006.01) |
| *C07D 257/00* | (2006.01) |
| *C08G 18/42* | (2006.01) |
| *C07F 5/06* | (2006.01) |
| *C08G 79/10* | (2006.01) |
| *C08G 77/04* | (2006.01) |
| *C08F 110/06* | (2006.01) |
| *C08G 18/76* | (2006.01) |

(52) U.S. Cl.
CPC .............. *C07F 5/069* (2013.01); *C08F 110/06* (2013.01); *C08G 18/42* (2013.01); *C08G 18/7621* (2013.01); *C08G 77/04* (2013.01); *C08G 79/10* (2013.01)

(58) Field of Classification Search
None
See application file for complete search history.

(56) References Cited

U.S. PATENT DOCUMENTS 5,589,595 A * 12/1996 Sandnes ............... C07D 257/02
  424/9.323
2009/0030120 A1   1/2009 Zijp et al.

FOREIGN PATENT DOCUMENTS

JP    H0481469 A    3/1992

OTHER PUBLICATIONS

Jiang, et al. "Synthesis Structure and Pyrolysis of Organoaluminum Amides Derivede from Reactions of Trialkylaluminium compounds with Ethylenediamine in a 3:2 ratio" Inorganic Chemistry, 30(5), 995-1000, Mar. 1, 1991.*
Aluminium nitride, http://en.wikipedia.org/wiki/Aluminium_nitride, May 12, 2014.
Janssen et al., Thermally-conductive plastics: balancing material properties with application needs, *Compounding World* (Feb. 2010), pp. 38-42.
Lu et al., Aluminum phthalocyanine complex covalently bonded to MCM-41 silica as heterogeneous catalyst for the synthesis of cyclic carbonates, *Journal of Molecular Catalysis A: Chemical*, (Jul. 2002), 186(1-2):33-42.
Sauls et al., Coordination compounds of aluminum as precursors to aluminium nitride, *Coordination Chemistry Reviews*, (1993), 128:193-207.
Sherman, Hot topic: adding thermal conductivity to plastics, *Compounding World* (Feb. 2010), pp. 28-36.
Xu et al., Increasing the thermal conductivity of boron nitride and aluminum nitride particle epoxy-matrix composites by particle surface treatments, *Composite Interfaces*, (2000), 7(4):243-256.
Xu et al., Thermally conducting aluminum nitride polymer-matrix composites, *Composites: Part A* (2001), 32:1749-1757.
Thermal Conductivity, accessed at https://web.archive.org/web/20160121075719/http://hyperphysics.phy-astr.gsu.edu/hbase/tables/thrcn.html, accessed on Feb. 2, 2016, pp. 2.
Alzeer et al., An efficient two-step synthesis of metal-free phthalocyanines using a Zn(II) template, Chemical communications, (15) pp. 1970-1971 (2009).
Saravanan et al., Dielectric and Conductivity Studies on Cobalt Phthalocyanine Tetramers, Journal of Applied Polymer Science, 91, pp. 2529-2535 (2004).
Thomas, Electro-Optical Propeties of Metal Phthalocyanines and Naphthalocyanines, Department of Applied Chemistry, Cochin University of Science and Technology, pp. 140 (Dec. 1995).

* cited by examiner

*Primary Examiner* — Randy Gulakowski
*Assistant Examiner* — Christopher M Rodd
(74) *Attorney, Agent, or Firm* — Pepper Hamilton LLP

(57) ABSTRACT

Thermal conductive compositions, methods for their preparation, and use are provided, which include, for example, as thermal sinks and other uses.

19 Claims, No Drawings

THERMAL CONDUCTIVE COMPOSITIONS AND METHODS FOR THEIR PREPARATION AND USE

BACKGROUND

A thermal sink that uses a thermal conductive matrix is one of the common requirements for electronic applications to dissipate the heat generated during operation of the encapsulated microelectronics in the polymer matrix. Metals can act as good thermal conductors, however, because they are also good electrical conductors they are not very useful as thermal sinks. On the other hand, polymer matrices can act as electrical insulators but are very poor thermal conductors and accordingly when the temperature rises the polymer will thermally decompose and not function as a thermal sink.

Accordingly, there is a need for compositions that can function as thermal sinks with better properties than what are currently available. The present disclosure overcomes at least some, or all of the disadvantages of previous compositions as well as provides other advantages as discussed herein.

SUMMARY

In some embodiments, thermal conductive compositions are provided. In some embodiments, the thermal conductive compositions comprising least one of a compound of Formula (I):

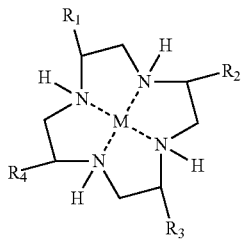
(I)

wherein:
M is Al, Ga, Si, Ge, In, or Sn;
$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$ $^-$OH, —CH$_2$CH(O)CH$_2$, —Si(R$_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H,
wherein:
X is halo;
$R_5$ is $C_1$-$C_6$ alkyl;
and a compound of Formula (II):

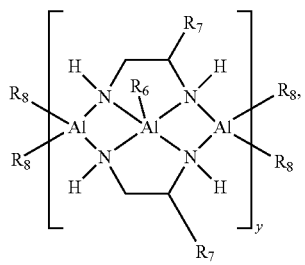
(II)

wherein:
y is about 10 to about 500;
$R_6$ is $C_1$-$C_6$ alkyl or halo;
each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$ $^-$OH, —CH$_2$CH(O)CH$_2$, —Si(R$_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo.

In some embodiments, the composition is a siloxane polymer cross linked or cured with a compound of Formula (I) or (II). In some embodiments, the siloxane polymer cured or cross linked with a compound of Formula (I) or (II) has a formula of:

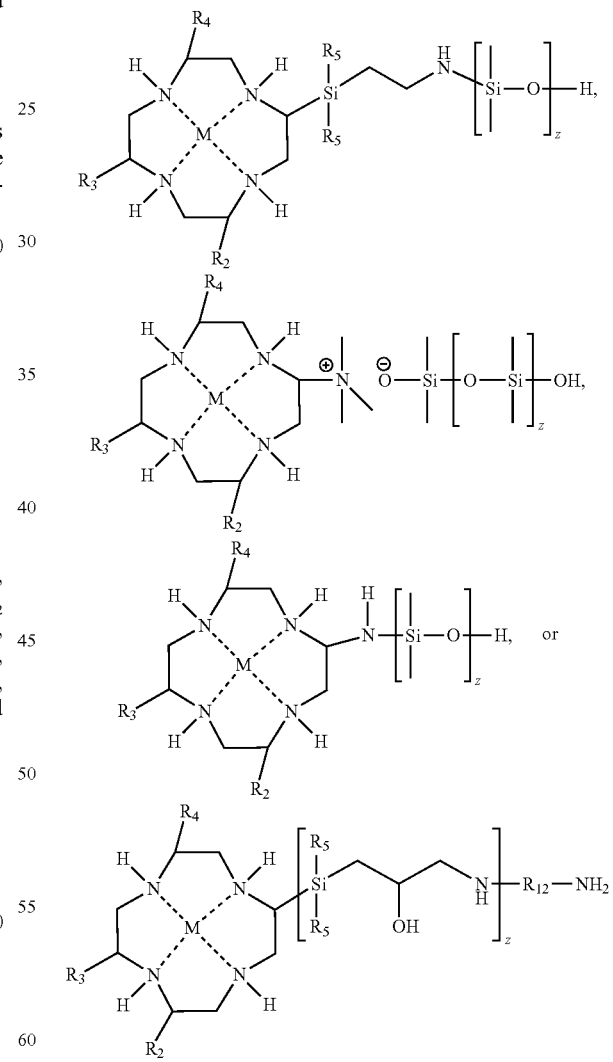

wherein
each $R_{12}$ is alkenyl, alkenylaryl, aryl or alicyclic; and
each z is independently about 1 to about 100.

In some embodiments, the composition is a polyurethane cross linked with a compound of Formula (I) or (II). In some embodiments, the polyurethane cross linked with a compound of Formula (I) or (II) is a compound of Formula (III):

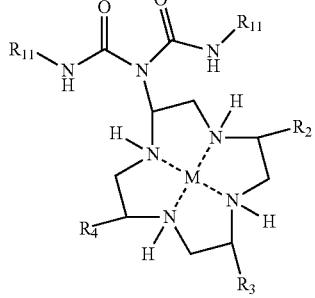
(III)

wherein:

M is Al, Ga, Si, Ge, In, or Sn;

$R_2$, $R_3$, and $R_4$ are each independently —H, or —$NH_2$, —Si(O$R_5$)$_3$, —Si(O$R_5$)$_2$CH$_2$CH$_2$NH$_2$, —Si($R_5$)$_2$CH$_2$CH$_2$NH$_2$, —N$^+$(CH$_3$)$_3$$^-$OH, —CH$_2$CH(O)CH$_2$, —Si($R_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O);

wherein:

X is halo;

$R_5$ is $C_1$-$C_6$ alkyl; and $R_{11}$ is a polyurethane chain.

In some embodiments, the composition is a polyolefin copolymerized or grafted with a compound of Formula (I) or (II). In some embodiments, the composition has a formula of:

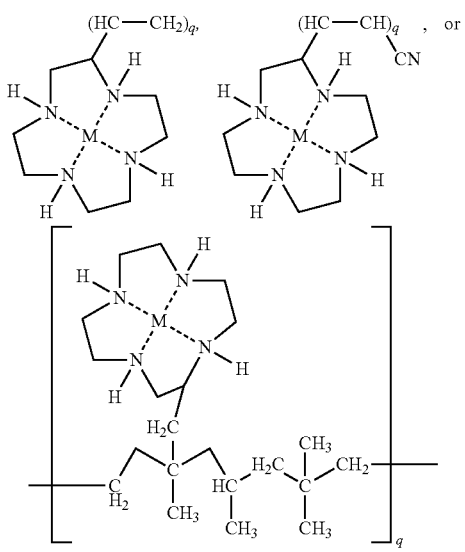

wherein

M is Al, Ga, Si, Ge, In, or Sn; and q is about 100 to about 10000.

In some embodiments heat sinks comprising at least one of a compound of Formula (I) are provided:

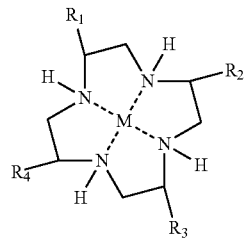
(I)

wherein:

M is Al, Ga, Si, Ge, In, or Sn;

$R_1$, $R_2$, $R_3$, and $R_4$ are each independently —H, or —$NH_2$, —Si(O$R_5$)$_3$, —Si(O$R_5$)$_2$CH$_2$CH$_2$NH$_2$, —Si($R_5$)$_2$CH$_2$CH$_2$NH$_2$, —N$^+$(CH$_3$)$_3$$^-$OH, —CH$_2$CH(O)CH$_2$, —Si($R_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H, wherein:

X is halo;

$R_5$ is $C_1$-$C_6$ alkyl;

and a compound of Formula (II):

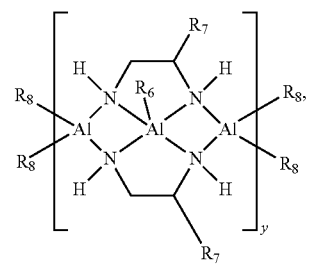
(II)

wherein:

y is about 10 to about 500;

$R_6$ is $C_1$-$C_6$ alkyl or halo;

each $R_7$ is independently —H, or —$NH_2$, —Si(O$R_9$)$_3$, —Si(O$R_9$)$_2$CH$_2$CH$_2$NH$_2$, —Si($R_9$)$_2$CH$_2$CH$_2$NH$_2$, —N$^+$(CH$_3$)$_3$$^-$OH, —CH$_2$CH(O)CH$_2$, —Si($R_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;

$R_8$ is —NH—CH$_2$—CH$_2$—NH$_2$ or Al($R_{10}$)$_2$;

$R_9$ is $C_1$-$C_6$ alkyl; and $R_{10}$ is $C_1$-$C_6$ alkyl or halo.

In some embodiments, heat transfer systems are provided. In some embodiments, the heat transfer systems comprise at least one heat source; at least one heat sink; and at least one thermal conductive composition comprising at least one of a compound of Formula (I)

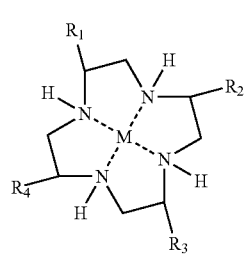
(I)

wherein:

M is Al, Ga, Si, Ge, In, or Sn;

$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, —CH(═O), provided that $R_1$, $R_2$, $R_3$, and $R_4$ are not all H, wherein:

X is halo;

$R_5$ is $C_1$-$C_6$ alkyl;

or a compound of Formula (II):

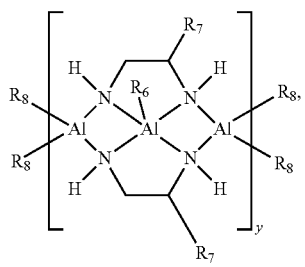

(II)

wherein:

y is about 10 to about 500

$R_6$ is $C_1$-$C_6$ alkyl or halo;

each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, or —CH(═O), provided that each $R_7$ are not both H;

$R_8$ is —NH—CH$_2$—CH$_2$—NH$_2$ or Al(R$_{10}$)$_2$;

$R_9$ is $C_1$-$C_6$ alkyl; and $R_{10}$ is $C_1$-$C_6$ alkyl or halo, wherein at least a portion of the thermal conductive composition is positioned substantially between the heat source and the heat sink and provides thermal communication between the heat source and heat sink.

Embodiments disclosed herein provide electronic devices, the electronic devices at least partially encapsulated by a thermal conductive composition comprising at least one of a compound of Formula (I):

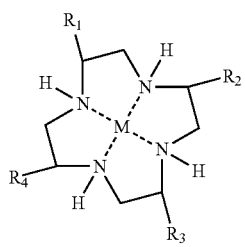

(I)

wherein:

M is Al, Ga, Si, Ge, In, or Sn;

$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, —CH(═O), provided that $R_1$, $R_2$, $R_3$, and $R_4$ are not all H, wherein:

X is halo;

$R_5$ is $C_1$-$C_6$ alkyl;

and a compound of Formula (II):

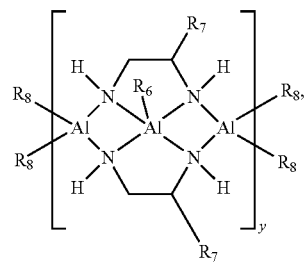

(II)

wherein:

y is about 10 to about 500;

$R_6$ is $C_1$-$C_6$ alkyl or halo;

each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, or —CH(═O), provided that each $R_7$ are not both H;

$R_8$ is —NH—CH$_2$—CH$_2$—NH$_2$ or Al(R$_{10}$)$_2$;

$R_9$ is $C_1$-$C_6$ alkyl; and $R_{10}$ is $C_1$-$C_6$ alkyl or halo.

In some embodiments, methods of preparing a polyurethane cross-linked compound of Formula (I) or (II) are provided, the methods comprising contacting a compound of Formula (I) or Formula (II)

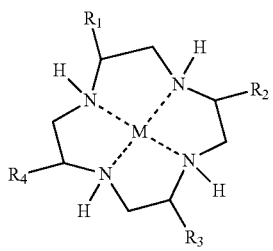

(I)

wherein:

M is Al, Ga, Si, Ge, In, or Sn;

$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, —CH(═O), provided that $R_1$, $R_2$, $R_3$, and $R_4$ are not all H, wherein:

X is halo;

$R_5$ is $C_1$-$C_6$ alkyl;

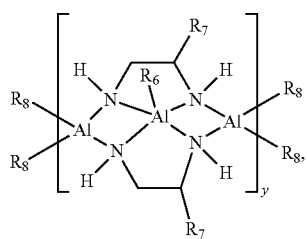

wherein:
y is about 10 to about 500;
$R_6$ is $C_1$-$C_6$ alkyl or halo;
each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, or —CH(═O), provided that each $R_7$ are not both H;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with a diisocyanate and a polyol under conditions sufficient to form a polyurethane cross-linked compound of Formula (I) or (II).

In some embodiments, methods of preparing a siloxane polymer cross linked or cured with a compound of Formula (I) or (II) are provided, the method comprising contacting a compound of Formula (I) or (II)

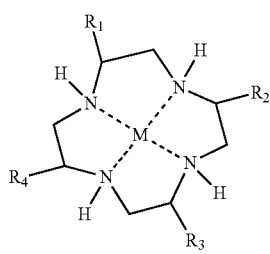

wherein:
M is Al, Ga, Si, Ge, In, or Sn;
$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, —CH(═O), provided that $R_1$, $R_2$, $R_3$, and $R_4$ are not all H,
wherein:
X is halo;
$R_5$ is $C_1$-$C_6$ alkyl;

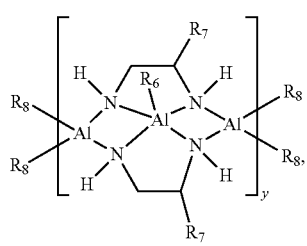

wherein:
y is about 10 to about 500;
$R_6$ is $C_1$-$C_6$ alkyl or halo;
each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, or —CH(═O), provided that each $R_7$ are not both H;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with a siloxane cyclic monomer or silicone oil in the presence of a crosslinking agent to form the siloxane polymer cross linked or cured with a compound of Formula (I) or (II).

In some embodiments, methods of preparing a polyolefin copolymerized or grafted with a compound of Formula (I) or (II) are provided, the methods comprising contacting a compound of a compound of Formula (I) or (II)

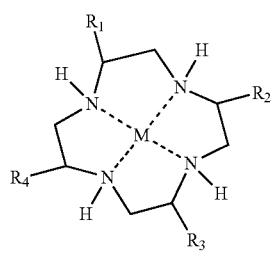

wherein:
M is Al, Ga, Si, Ge, In, or Sn;
$R_1$, $R_2$, $R_3$, and $R_4$ are each independently —CH$_2$═CH—, CH$_2$═CH CH$_2$—, or —CH$_2$═CH(CN),
wherein:
X is halo;
$R_5$ is $C_1$-$C_6$ alkyl;

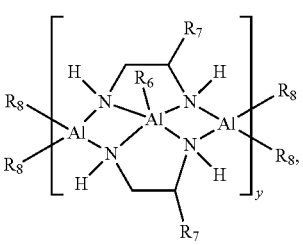

wherein:
y is about 10 to about 500;
$R_6$ is $C_1$-$C_6$ alkyl or halo;
each $R_7$ is independently CH$_2$═CH—, or CH$_2$═CHCH$_2$—, or CH$_2$═CH(CN)—;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with an olefin monomer under conditions suitable for free radical polymerization or anionic polymerization.

In some embodiments, methods of preparing a polyolefin grafted with a compound of Formula (I) or (II) are provided, the methods comprising contacting a polyolefin with a compound of Formula (I) or (II),

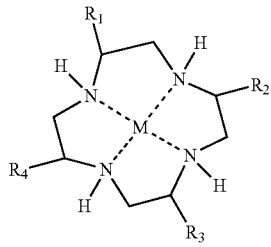

wherein:
M is Al, Ga, Si, Ge, In, or Sn;
$R_1$, $R_2$, $R_3$, and $R_4$ are —$CH_3$,
wherein:
X is halo;
$R_5$ is $C_1$-$C_6$ alkyl;

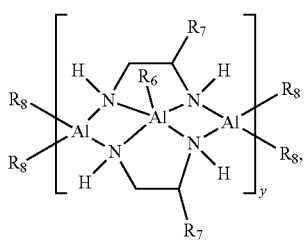

wherein:
y is about 10 to about 500;
$R_6$ is $C_1$-$C_6$ alkyl or halo;
$R_7$ is —$CH_3$;
$R_8$ is —NH—$CH_2$—$CH_2$—$NH_2$ or Al($R_{10}$)$_2$;
$R_9$ is $C_1$-$C_6$ alkyl; and
$R_{10}$ is $C_1$-$C_6$ alkyl or halo,
in the presence of a peroxide in a reactive extruder.

DETAILED DESCRIPTION

This description is not limited to the particular processes, compositions, or methodologies described, as these may vary. The terminology used in the description is for the purpose of describing the particular versions or embodiments only, and it is not intended to limit the scope of the embodiments described herein. Unless defined otherwise, all technical and scientific terms used herein have the same meanings as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

It must also be noted that as used herein and in the appended claims, the singular forms "a", "an", and "the" include plural reference unless the context clearly dictates otherwise.

As used herein, the term "alkyl" means a saturated or unsaturated hydrocarbon group which is straight-chained or branched. An unsaturated alkyl group refers to an alkyl group that contains at least one double bond, which can also be referred to as an "alkenyl." The alkyl chain can also be substituted. An alkyl group can contain from 1 to 24, from 1 to 22, from 1 to 20, from 1 to 18, from 1 to 16, from 1 to 14, from 1 to 12, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (for example, n-propyl and isopropyl), butyl (for example, n-butyl, t-butyl, isobutyl), pentyl (for example, n-pentyl, isopentyl, neopentyl), hexyl, isohexyl, heptyl, 4,4 dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the phrase "$C_1$-$C_{24}$ alkyl, optionally comprising at least one alkenyl group" refers to a $C_1$-$C_{24}$ alkyl carbon chain that can have at least one alkenyl group located anywhere in the chain. When the $C_1$-$C_{24}$ alkyl carbon chain has at least one alkenyl group, the length of the $C_1$-$C_{24}$ alkyl carbon chain is at least two carbons. When present, the carbons in the alkenyl group are counted as carbons in the $C_1$-$C_{24}$ alkyl carbon chain.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 24 carbon atoms in length, from 2 to 22 carbon atoms in length, from 2 to 20 carbon atoms in length, from 2 to 18 carbon atoms in length, from 2 to 16 carbon atoms in length, from 2 to 14 carbon atoms in length, from 2 to 12 carbon atoms in length, from 2 to 10 carbon atoms in length, from 2 to 8 carbon atoms in length, from 2 to 6 carbon atoms in length, or from 2 to 4 carbon atoms in length. In some embodiments, the alkenyl group has 1, 2, 3, 4, 5, or 6 double bonds.

As used herein, the term "alkenylaryl" refers to an alkenyl group substituted with an aryl group.

As used in this document, terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Embodiments disclosed herein provide new thermal conductors that can act, for example, as heat sinks.

In some embodiments, a thermal conductive composition is provided. In some embodiments, the thermal conductive composition includes at least one of a compound of Formula (I):

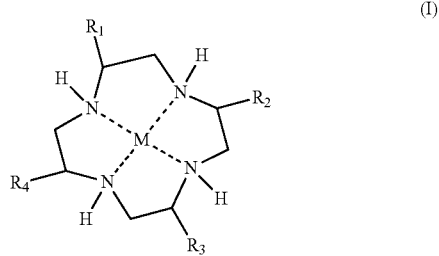

wherein:

M is Al, Ga, Si, Ge, In, or Sn;

$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H, wherein:

X is halo;

$R_5$ is C$_1$-C$_6$ alkyl;

or a compound of Formula (II):

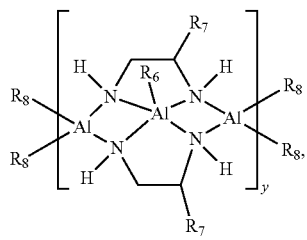

(II)

wherein:

y=about 10 to about 500;

$R_6$ is C$_1$-C$_6$ alkyl or halo;

each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;

$R_8$ is —NH—CH$_2$—CH$_2$—NH$_2$ or Al(R$_{10}$)$_2$;

$R_9$ is C$_1$-C$_6$ alkyl; and $R_{10}$ is C$_1$-C$_6$ alkyl or halo.

In some embodiments, y is about 10, about 50, about 100, about 150, about 200, about 250, about 300, about 350, about 400, about 450, about 500, or a value between any of these values.

In some embodiments, the metal, M, is Al.

In some embodiments, $R_1$, $R_2$, $R_3$, and $R_4$ are each independently H, or NH$_2$, —Si(OR$_5$)2CH$_2$CH$_2$NH$_2$, Si(OR$_5$)$_3$, N(CH$_3$)$_3$OH, CH$_2$CH(O)CH$_2$, —CH$_3$, —CH=CH$_2$, —CH$_2$CH=CH$_2$, —CH$_2$CH(O)CH$_2$, —CH=CH—CN, —OCN, —CH$_2$OH, CH$_2$Cl, CH$_2$OCN, or —CH(=O). In some embodiments, none of $R_1$, $R_2$, $R_3$, and $R_4$ are H.

In some embodiments, at least one of $R_1$, $R_2$, $R_3$, and $R_4$ is Si(R$_5$)$_2$CH$_2$CH$_2$NH$_2$, Si(OR$_5$)$_2$CH$_2$CH$_2$NH$_2$, or Si(OR$_5$)$_3$. In some embodiments, at least one of $R_1$, $R_2$, $R_3$, and $R_4$ is Si(OR$_5$)$_2$CH$_2$CH$_2$NH$_2$, or Si(OR$_5$)$_3$.

In some embodiments, $R_7$ is H, or NH$_2$, —Si(OR$_9$)$_2$CH$_2$CH$_2$NH$_2$, Si(OR$_9$)$_3$, —N$^+$(CH$_3$)$_3$$^-$OH, CH$_2$CH(O)CH$_2$, —CH$_3$, —CH=CH$_2$, —CH$_2$CH=CH$_2$, —CH$_2$CH(O)CH$_2$, —CH=CH—CN, —OCN, —CH$_2$OH, CH$_2$Cl, CH$_2$OCN, or —CH(=O). In some embodiments, $R_7$ is —Si(R$_9$)$_2$CH$_2$CH$_2$NH$_2$.

In some embodiments, the composition is a siloxane polymer cross linked or cured with a compound of Formula (I) or (II). In some embodiments, the siloxane polymer cured or cross linked with a compound of Formula (I) or (II) has a formula of:

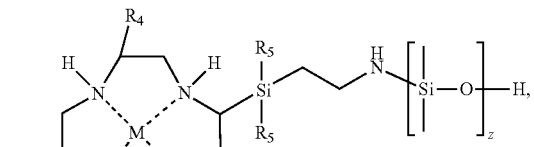

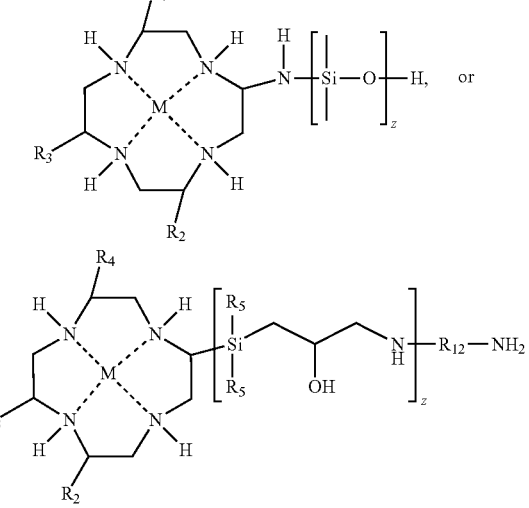

wherein each $R_{12}$ is alkenyl, alkenylaryl, aryl or alicyclic; and each z is independently about 10 to about 1000.

In some embodiments, z is about 10, about 100, about 200, about 300, about 400, about 500, about 600, about 700, about 800, about 900, about 1000, or a value between any of these values.

In some embodiments, the composition is a polyurethane cross linked with a compound of Formula (I) or (II). In some embodiments, the polyurethane cross linked with a compound of Formula (I) or (II) is a compound of Formula (III):

(III)

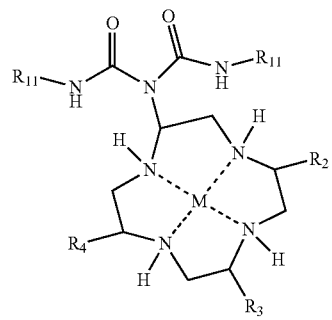

wherein:

M is Al, Ga, Si, Ge, In, or Sn;

$R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3{}^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH-CN$, —$OCN$, —$CH_2OH$, $CH_2X$, $CH_2OCN$, —$CH(=O)$;

wherein:

X is halo;

$R_5$ is $C_1$-$C_6$ alkyl; and $R_{11}$ is a polyurethane chain.

In some embodiments, the composition is a polyolefin copolymerized or grafted with a compound of Formula (I) or (II). In some embodiments, the composition has a formula of:

wherein

M is Al, Ga, Si, Ge, In, or Sn; and q is about 100 to about 10000.

In some embodiments, q is about 100, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, or a value between any of these values.

In some embodiments, the compositions described herein have a thermal conductivity of about 10 W/(m.K) to about 50 W/(m.K). In some embodiments, the compositions described herein have a thermal conductivity of about 10 W/(m.K), about 20 W/(m.K), about 30 W/(m.K), about 40 W/(m.K), about 50 W/(m.K), or a thermal conductivity between any of these values.

Heat sinks are also provided herein. A heat sink is generally a passive heat exchanger that cools a device by dissipating heat from a system that generates heat through its normal function into the surrounding medium. For example, heat sinks are often used to cool CPUs in a computer. The compositions described herein can be used as heat sinks, amongst other uses.

Accordingly, in some embodiments, a heat sink is provided, wherein the heat sink comprises at least one of a compound of Formula (I):

wherein:

M is Al, Ga, Si, Ge, In, or Sn;

$R_1$, $R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3{}^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH-CN$, —$OCN$, —$CH_2OH$, $CH_2X$, $CH_2OCN$, —$CH(=O)$, provided that $R_1$, $R_2$, $R_3$, and $R_4$ are not all H, wherein:

X is halo;

$R_5$ is $C_1$-$C_6$ alkyl;

or a compound of Formula (II):

wherein:

y is about 10 to about 500;

$R_6$ is $C_1$-$C_6$ alkyl or halo;

each $R_7$ is independently —H, or —$NH_2$, —$Si(OR_9)_3$, —$Si(OR_9)_2CH_2CH_2NH_2$, —$Si(R_9)_2CH_2CH_2NH_2$, —$N^+(CH_3)_3{}^-OH$, —$CH_2CH(O)CH_2$, —$Si(R_9)_2CH_2CH(O)CH_2$, —$CH_3$, —$CH=CH_2$, —$CH_2CH=CH_2$, —$CH=CH-CN$, —$OCN$, —$CH_2OH$, $CH_2X$, $CH_2OCN$, or —$CH(=O)$, provided that each $R_7$ are not both H;

$R_8$ is —$NH-CH_2-CH_2-NH_2$ or $Al(R_{10})_2$;

$R_9$ is $C_1$-$C_6$ alkyl; and $R_{10}$ is $C_1$-$C_6$ alkyl or halo. In some embodiments, y is about 10, about 50, about 100, about 150, about 200, about 250, about 300, about 350, about 400, about 450, about 500, or a value between any of these values.

In some embodiments of the heat sink, the metal, M, is Al. In some embodiments, $R_1$ is —$CH_3$, —$CH_2CH_3$, or halo. In some embodiments, $R_1$ is $Si(R_5)_2CH_2CH_2NH_2$. In some embodiment of the heat sink, $R_7$ is H, —$NH_2$, —$Si(OR_9)_2CH_2CH_2NH_2$, —$Si(OR_9)_3$, —$N^+(CH_3)_3{}^-OH$, —$CH_2CH(O)CH_2$, —$CH_3$, —$CH=CH_2$, —$CH_2CH=CH_2$, —$CH_2CH(O)CH_2$, —$CH=CHCN$, —$OCN$, —$CH_2OH$, —$CH_2Cl$, —$CH_2OCN$, —$CH(=O)$. In some embodiments, $R_7$ is —$Si(R_9)_2CH_2CH_2NH_2$.

In some embodiments, the heat sink comprises a siloxane polymer cured or cross linked with a compound of Formula (I) or (II). In some embodiments, the siloxane polymer cured or cross linked with a compound of Formula (I) or (II) a formula of:

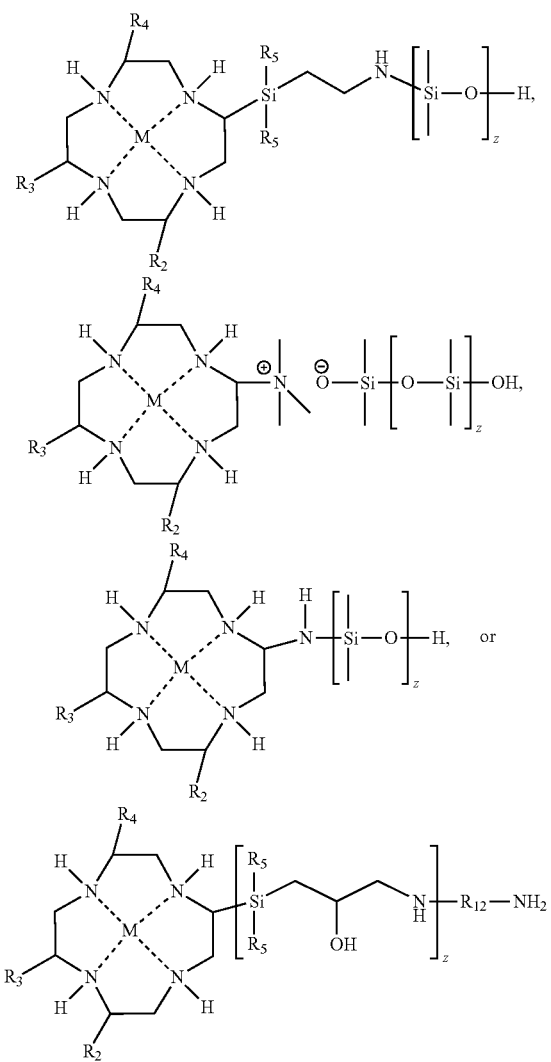

wherein
each $R_{12}$ is alkenyl, alkenylaryl, aryl or alicyclic; and
each z is independently about 10 to about 1000.

In some embodiments, z is about 10, about 100, about 200, about 300, about 400, about 500, about 600, about 700, about 800, about 900, about 1000, or a value between any of these values.

In some embodiments, the heat sink comprises a polyurethane cross linked with a compound of Formula (I) or (II). In some embodiments, the polyurethane cross linked with a compound of Formula (I) or (II) is a compound of Formula (III):

(III)

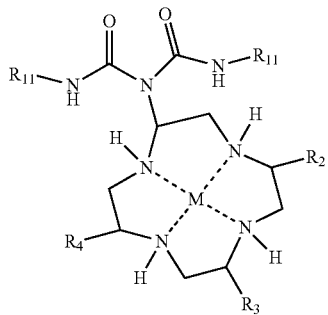

wherein:

M is Al, Ga, Si, Ge, In, or Sn;

$R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O);

wherein:

X is halo;

$R_5$ is $C_1$-$C_6$ alkyl; and $R_{11}$ is a polyurethane chain.

In some embodiments, the heat sink comprises a polyolefin copolymerized or grafted with a compound of Formula (I) or (II). In some embodiments, the polyolefin copolymerized or grafted with a compound of Formula (I) or (II) has a formula of:

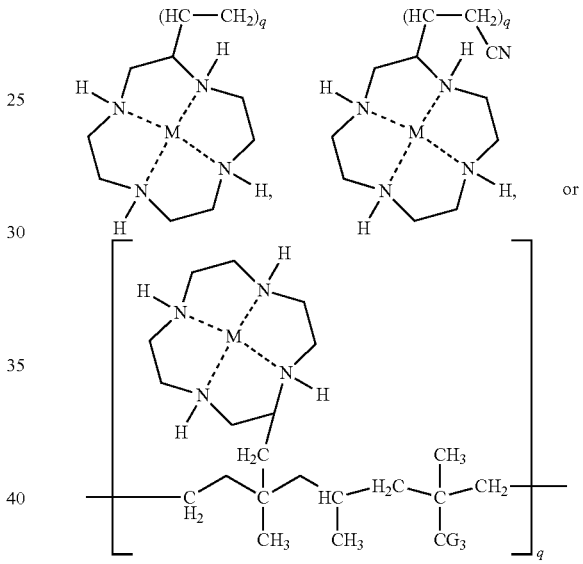

wherein

M is Al, Ga, Si, Ge, In, or Sn; and q is about 100 to about 10000. In some embodiments, q is about 100, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, or a value between any of these values.

In some embodiments, the heat sinks described herein are configured to have a thermal conductivity of about 10 W/(m.K) to about 50 W/(m.K). In some embodiments, the heatsinks described herein are configured to have a thermal conductivity of about 10 W/(m.K), about 20 W/(m.K), about 30 W/(m.K), about 40 W/(m.K), about 50 W/(m.K), or a thermal conductivity between any of these values.

In some embodiments, a heat transfer system comprising at least one heat source; at least one heat sink; and at least one thermal conductive composition are provided. In some embodiments, the at least one thermal conductive composition comprises includes at least one of a compound of Formula (I):

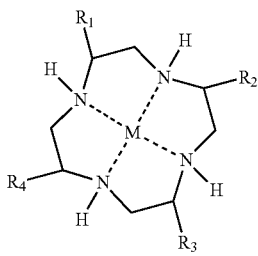

wherein:

M is Al, Ga, Si, Ge, In, or Sn;

$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, —CH(═O), provided that $R_1$, $R_2$, $R_3$, and $R_4$ are not all H, wherein:

X is halo;

$R_5$ is $C_1$-$C_6$ alkyl;

or a compound of Formula (II):

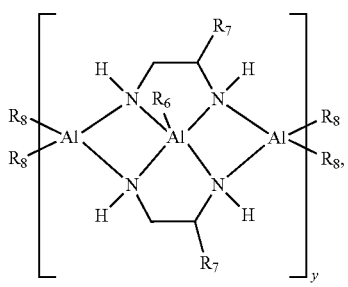

wherein:

y is about 10 to about 500;

$R_6$ is $C_1$-$C_6$ alkyl or halo;

each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH═CH$_2$, —CH$_2$CH═CH$_2$, —CH═CH—CN, —OCN, —CH$_2$OH, CH$_2$X, CH$_2$OCN, or —CH(═O), provided that each $R_7$ are not both H;

$R_8$ is —NH—CH$_2$—CH$_2$—NH$_2$ or Al(R$_{10}$)$_2$;

$R_9$ is $C_1$-$C_6$ alkyl; and $R_{10}$ is $C_1$-$C_6$ alkyl or halo;

wherein at least a portion of the thermal conductive composition is positioned substantially between the heat source and the heat sink and provides thermal communication between the heat source and heat sink. In some embodiments, M is Al. In some embodiments, y is about 10, about 50, about 100, about 150, about 200, about 250, about 300, about 350, about 400, about 450, about 500, or a value between any of these values.

In some embodiments of the heat transfer system, $R_1$, $R_2$, $R_3$, and $R_4$ are each independently H, or NH$_2$, —Si(OR$_5$)$_2$CH$_2$CH$_2$NH$_2$, Si(OR$_5$)$_3$, N(CH$_3$)$_3$OH, CH$_2$CH(O)CH$_2$, —CH$_3$, —CH═CH$_2$, —CH$_2$CH═CH$_2$, —CH$_2$CH(O)CH$_2$, —CH═CH—CN, —OCN, —CH$_2$OH, CH$_2$Cl, CH$_2$OCN, or —CH(═O).

In some embodiments of the heat transfer system, $R_7$ is H, or NH$_2$, —Si(OR$_9$)$_2$CH$_2$CH$_2$NH$_2$, Si(OR$_9$)$_3$, —N$^+$(CH$_3$)$_3$$^-$OH, CH$_2$CH(O)CH$_2$, —CH$_3$, —CH═CH$_2$, —CH$_2$CH═CH$_2$, —CH$_2$CH(O)CH$_2$, —CH═CH—CN, —OCN, —CH$_2$OH, CH$_2$Cl, CH$_2$OCN, or —CH(═O).

In some embodiments of the heat transfer system, the thermal conductive composition is a siloxane polymer cross linked with a compound of Formula (I) or (II). In some embodiments, the siloxane polymer cured or cross linked with a compound of Formula (I) or (II) has a formula of:

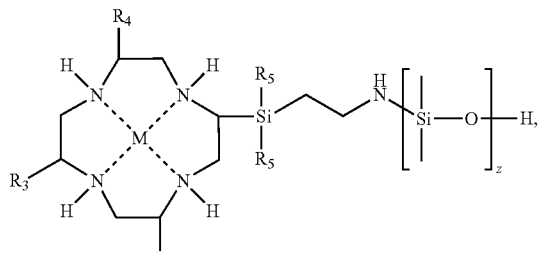

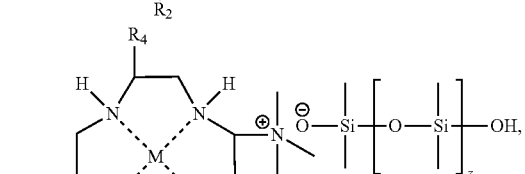

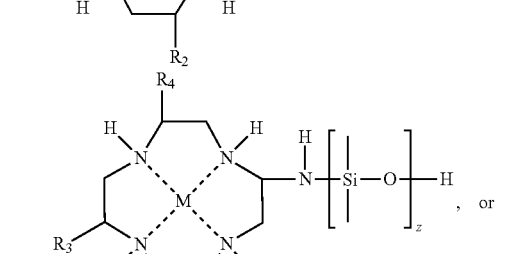

, or

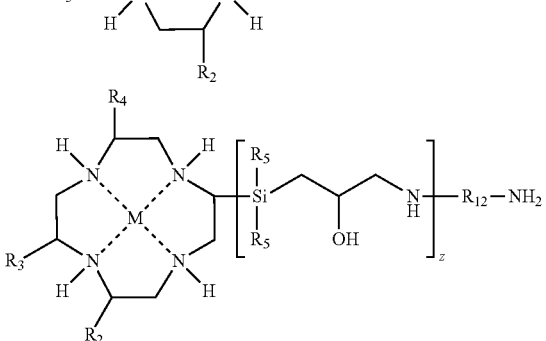

wherein each $R_{12}$ is alkenyl, alkenylaryl, aryl or alicyclic; and each z is independently about 10 to about 1000.

In some embodiments, z is about 10, about 100, about 200, about 300, about 400, about 500, about 600, about 700, about 800, about 900, about 1000, or a value between any of these values.

In some embodiments, electronic devices that are at least partially encapsulated by a thermal conductive composition are provided. In some embodiments, the thermal conductive composition comprises at least one of a compound of Formula (I):

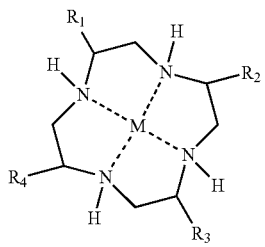

(I)

wherein:
M is Al, Ga, Si, Ge, In, or Sn;
$R_1$, $R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH—CN$, —OCN, —$CH_2OH$, $CH_2X$, $CH_2OCN$, —$CH(=O)$, provided that $R_1$, $R_2$, $R_3$, and $R_4$ are not all H,
wherein:
X is halo;
$R_5$ is $C_1$-$C_6$ alkyl;
or a compound of Formula (II):

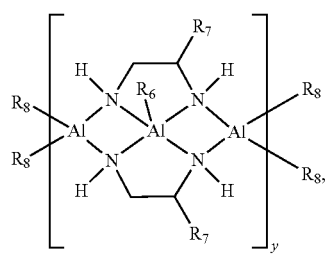

(II)

wherein:
y is about 10 to about 500;
$R_6$ is $C_1$-$C_6$ alkyl or halo;
each $R_7$ is independently —H, or —$NH_2$, —$Si(OR_9)_2$, —$Si(OR_9)_2CH_2CH_2NH_2$, —$Si(R_9)_2CH_2CH_2NH_2$, —$N^+(CH_3)_3^-OH$, —$CH_2CH(O)CH_2$, —$Si(R_9)_2CH_2CH(O)CH_2$, —$CH_3$, —$CH=CH_2$, —$CH_2CH=CH_2$, —$CH=CH—CN$, —OCN, —$CH_2OH$, $CH_2X$, $CH_2OCN$, or —$CH(=O)$, provided that each $R_7$ are not both H;
$R_8$ is —$NH—CH_2—CH_2—NH_2$ or $Al(R_{10})_2$;
$R_9$ is $C_1$-$C_6$ alkyl; and
$R_{10}$ is $C_1$-$C_6$ alkyl or halo.

In some embodiments, M is Al. In some embodiments, y is about 10, about 50, about 100, about 150, about 200, about 250, about 300, about 350, about 400, about 450, about 500, or a value between any of these values.

In some embodiments of the electronic device, the thermal composition is as described above, wherein $R_1$, $R_2$, $R_3$, and $R_4$ are each independently H, or $NH_2$, —$Si(OR_5)_2CH_2CH_2NH_2$, $Si(OR_5)_2$, $N(CH_3)_3OH$, $CH_2CH(O)CH_2$, —$CH_3$, —$CH=CH_2$, —$CH_2CH=CH_2$, —$CH_2CH(O)CH_2$, —$CH=CH—CN$, —OCN, —$CH_2OH$, $CH_2Cl$, $CH_2OCN$, or —$CH(=O)$. In some embodiments, $R_7$ is H, or $NH_2$, —$Si(OR_9)_2CH_2CH_2NH_2$, $Si(OR_9)_2$, —$N^+(CH_3)_3^-OH$, $CH_2CH(O)CH_2$, —$CH_3$, —$CH=CH_2$, —$CH_2CH=CH_2$, —$CH_2CH(O)CH_2$, —$CH=CH—CN$, —OCN, —$CH_2OH$, $CH_2Cl$, $CH_2OCN$, or —$CH(=O)$.

In some embodiment of the electronic device, the thermal composition is a siloxane polymer cross linked with a compound of Formula (I) or (II). In some embodiments, the siloxane polymer cured or cross linked with a compound of Formula (I) or (II) has a formula of:

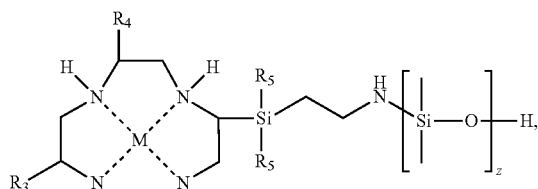

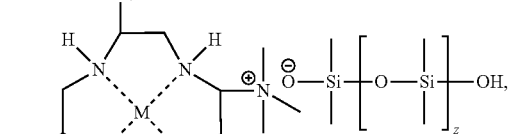

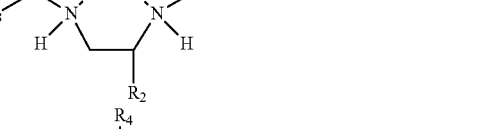

, or

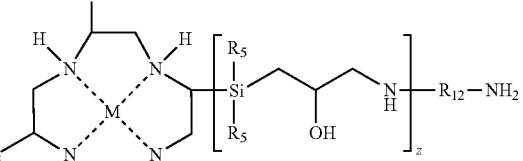

wherein
each $R_{12}$ is alkenyl, alkenylaryl, aryl or alicyclic; and
each z is independently about 10 to about 1000.

In some embodiments, the electronic device is encapsulated by the composition. Examples of electronic devices that can be partially or completely encapsulated by the thermal conductive compositions described herein, include, but are not limited to a semiconductor chip, a conductive wire, an electronic component, or an electronic circuit. However, other types of electronic devices can also be used in conjunctions with the compositions described herein and the types of device should not be limited unless explicitly limited by the present description.

The aza crown ethers of selective metals from group III and IV of periodic table can act as nano thermal conductive ingredients to replace commercial thermal conductive fillers when their structures are present as aza crown ether compounds, and/or as grafted on polymeric chains and/or as polymers and copolymers of aza crown ether complexes and or as master batch used with commercial polymers or in combination.

Methods of preparing the thermal compositions described herein are also provided. In some embodiments, compounds of Formula (I) or (II) as described herein are contacted with a siloxane cyclic monomer or silicone oil in the presence of active cross linking agents such as, but not limited to, $CH_3Si(OCH_2CH_3)_3$, $C_6H_5Si(OCH_3)_3$, $C_4H_9Si(OCH_3)_3$, $CH_2(O)CHCH_2Si(OCH_3)_3$, and $NH_2CH_2CH_2NHCH_2CH_2Si(OCH_3)_3$ under conditions sufficient to prepare the polymers described herein. In some embodiments, the compounds of Formula (I) or (II) are contacted with the siloxane cyclic monomer or the silicone oil in the presence of the cross linking agent under dry conditions at temperature of about 0-30° C. to form a siloxane polymers. The polymers can then be used as composites, sealants, and for encapsulating products, rubber and others uses as described herein. A non-limiting example of a siloxane cyclic monomer is

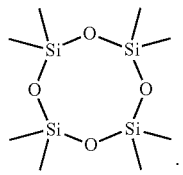

The derivative is formed, for example, by anionic ring opening polymerization of the siloxane cyclic monomer in the presence of anionic initiators such as, but not limited to $LiNH_2$, under, for example, dry conditions, in the presence of aprotic solvents. Examples of aprotic solvents include, but are not limited to, tetrahydrofuran, dioxane, trimethylamine, and the like. The reaction can take place at any suitable temperature, including but not limited to, a temperatures of about 0 to 30 C. Other siloxane derivatives can be formed by a compound of Formula (I) or (II), wherein $R_1$, $R_2$, $R_3$, $R_4$, and $R_7$ are each independently glycidyl ether groups (for example, such as but not limited to $CH_2(O)CHCH_2$—) with about an equivalent weight of an epoxy curing hardener (for example, amine compounds that contain active hydrogen) of the general formula $NH_2R_{12}NH_2$ wherein $R_{12}$ is alkenyl, alkenylaryl, aryl or alicyclic. In some embodiments, the reaction takes place at a temperature range of about 20-30 C. In some embodiments, the reaction includes the addition of at least one phenolic activator.

In some embodiments, the polyurethane cross linked with a compound of Formula (I) or (II) are prepared by contacting a compound of Formula (I) or (II), wherein $R_1$, $R_2$, $R_3$, $R_4$ and $R_7$ respectively as described herein with

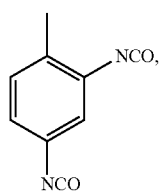

or other commercial diisocyanate compounds which can also be referred to as toluene-2,4-diisocyanate, and

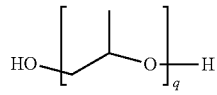

or $HO\{-R_{13}-O-C(O)R_{14}-C(O)OR_{15}-O-\}_qH$, wherein $R_{13}$, $R_{14}$, or $R_{15}$ are independently $C_1$-$C_6$ alkyl and q is about 100 to about 1000. These compounds and can also be referred to as a polyol. The structures can also be referred to as polyether polyol or polyester polyol. Without wishing to be bound by any theory, the reaction occurs as the amino aza crown ether complexes act as catalyst and as crosslinking agent. The product that is formed can take shape of the mold.

In some embodiments, the polyolefins are prepared by copolymerizing compounds of formula (I) or (II), wherein $R_1$, $R_2$, $R_3$, $R_4$, and $R_7$ are vinyl groups such as, but not limited to, $CH_2=CH-$, or $CH_2=CH\ CH_2-$, or $CH_2=CH(CN)-$, with olefin monomers by free radical polymerization or anionic polymerization implementing standard well known procedures. Examples of olefin monomers include, but are not limited to, ethylene, propylene, acrylonitrile, vinylchloride, butadiene, and the like and those that are described herein.

In some embodiments, the polyolefin are grafted with a compound of Formula (I) or (II) are prepared by contacting a polyolefin (for example, polyethylene or polypropylene) with a compound of Formula (I) or (II), wherein $R_1$, $R_2$, $R_3$, $R_4$, and $R_7$ are $CH_3$ in the presence of di-t-butyl peroxide in a reactive extruder. Accordingly, the azacrown ether complexes can be grafted on the polyolefin chains. In some embodiments, the conditions include performing reactive extrusion, which can be performed in the presence of high decomposition temperature peroxides such as di-butyl peroxide.

The aza crown ether compounds can be prepared according to generally any method. Specific examples of making specific species are described herein. In some embodiments, the methods described herein are modified to yield the different species that are desired to be produced according to the substituent groups required to be linked with aza crown ether. In some embodiments, standard procedures are used by contacting the alkylene diamine or its derivatives with trialkyl metals (for example, $AlR_3$) or metal halides (for example, $AlCl_3$) under dry or extremely dry conditions. In some embodiments, cyclization to form aza crown ethers and their derivatives include performing the reaction in dilute solution and/or presence of catalyst as indicated in the examples described herein.

EXAMPLES

Example 1

Preparation of Poly (Aluminium Ethylenediamine) Aza Crown Ether Complexes

A three necked reaction vessel is fitted with a stirrer, a condenser connected to a drying tube packed with anhydrous calcium chloride, and a separating funnel equipped with a pressure equalizing tube immersed into an oil bath that is temperature controlled by a thermostat. The reaction vessel is charged with two moles of 1,2-ethylenediamine. A dropping funnel is charged with one mole of anhydrous tri-methyl aluminium (TMA). The reaction vessel is flushed with dry nitrogen for 10 minutes, and the TMA is added portion wise from the dropping funnel into the reaction vessel at a controlled temperature of 80° C. within one hour. The reactants in the reaction vessel are allowed to react overnight. Thereafter, unreacted TMA is separated from the product by adding methanol and water (1:1 volume ratio) into the reaction vessel to dissolve the unreacted TMA. The product is a viscous liquid that easily separates from the dissolved TMA. The product is then removed and dried to yield a low molecular weight polymer, which is set aside for characterization. The polymer is used as a curing agent for several commercial resins as shown in the following examples.

The same reaction procedure is repeated using TMA and ethylene diamine in 1:1 ratio under similar conditions. A solid high molecular weight polymer is obtained, purified and characterized. The polymer is used as curing agent for several commercial resins and or transferred to master batch.

The polymer that is produced according to this example can be represented by the formula of:

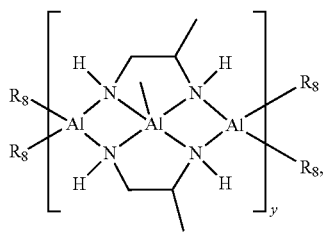

wherein $R_8$ is —NH—CH$_2$(CH$_3$)CH$_2$NH$_2$ and y is about 10 to about 500.

Example 2

Preparation of Methyl Derivatives of Aluminum Ethylenediamine Aza Crown Ether Complexes The same reaction set-up used in Example 1 is used in the preparation of aluminum ethylenediamine methyl derivative aza crown ether. One mole of trimethylaluminum is added portion wise to six moles of 1-methylethylenediamine (excess) at 80° C. The reaction is allowed to continue overnight. The obtained aluminum ethylenediamine azacrown ether complex is separated purified and characterized and used as a grafting agent to improve thermal conductivity of several commercial polymers. The procedure can be used to prepare a compound of the following formula:

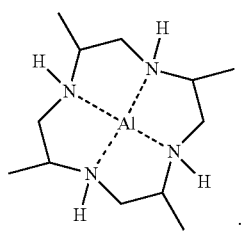

Example 3

Preparation of Amino Derivatives of Aluminum Ethylenediamine Aza Crown Ether Complexes (AAEDACE) (Formula (I))

The same reaction procedure and set-up used in Example 2 are implemented replacing 1-methylethylene diamine by 1-aminoethylenediamine. The obtained product is used as curing agent or crosslinking agent for several commercial resins.

Example 4

Production of Thermal Conductive Epoxy Resin Consisting Poly (Aluminum Ethylenediamine) Aza Crown Ether Complexes (PAEDACE)

100 g of liquid epoxy resin is mixed with 20 g of (PAEDACE), which can be prepared according to Example 1. The mixed resin is casted in glass dishes treated with silicon grease as a mold release and left overnight. The thermal conductivity of the solid cured discs are evaluated. Parallel sets of epoxy resins cured with ethylene diamine commercial product are prepared and evaluated for comparison.

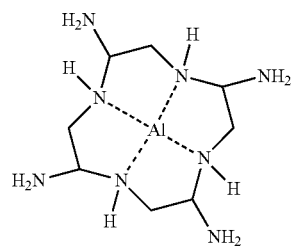

Example 5

A Compound of Formula (III) as a Curing and/or Crosslinking Agent for Polyurethane, Siloxane and Epoxy Resins 100 g of commercial liquid epoxy resin is mixed with 20 g of (PAEDACE), which can be prepared according to Example 1. The mixed resin is casted in glass dishes treated with silicon grease as mold release and an electrical circuit is encapsulated in the resin. The fully cured encapsulated samples are evaluated by measuring the break down voltage. Comparative set of encapsulated circuits in commercial epoxy resin cured with ethylene diamine are also prepared and evaluated for comparison.

Example 6

Preparation of Encapsulated Resin 100 g of commercial liquid epoxy resin is mixed with 20 g of (AAEDACE), which can be prepared according to Example 3. The mixed resin is casted in glass dishes treated with silicon grease as mold release and an electrical circuit is encapsulated in the resin. The fully cured encapsulated samples are evaluated by measuring the break down voltage. Comparative set of encapsulated circuits in commercial epoxy resin cured with ethylene diamine are also prepared and evaluated for comparison.

Example 7

Preparation of Encapsulated Electrical Circuit

Commercial polyurethane is prepared by curing 20 g of toluenediisocyanate with 20 g of polyesterpolyol, and 5 g of (PAEDACE), which can be prepared according to Example 1, and are mixed gently and used in encapsulation of electrical circuits. Pressure is applied to obtain a high density polyurethane encapsulated sample. Similar encapsulated electrical circuit samples in commercial polyurethane are prepared. The two samples are evaluated. The break down voltage is measured and higher breakdown voltage is indication of enhanced thermal conductivity. The procedure described herein can be modified by replacing PAEDACE with AAEDACE.

Example 8

Preparation of an Encapsulated Electrical Circuit in Thermal Conductive Silicon Rubber One mole of siloxane cyclic monomer is mixed with 0.1 mole of (PAEDACE), which can be prepared according to Example 1 in the presence of 0.01 mole of butyl-tris(glycidylether)siloxane as a crosslinking agent. The obtained resin is poured into a mold containing an electrical circuit. The sample is left to cure overnight and is evaluated via measuring the breakdown voltage. A similar sample is prepared by using commercial composition for silicon rubber. The sample is evaluated for comparison. It is expected that the material used herein performs better than the commercial composition for silicon rubber.

Specifically, a semiconductor chip is at least partially encapsulated by

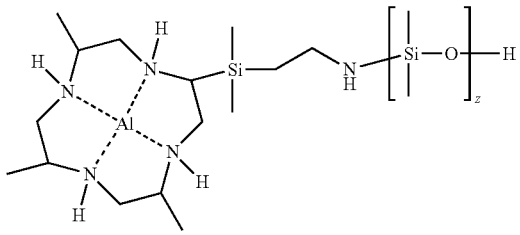

wherein z is 50, which can act to dissipate the heat away from the semiconductor chip. The composition can be prepared by contacting

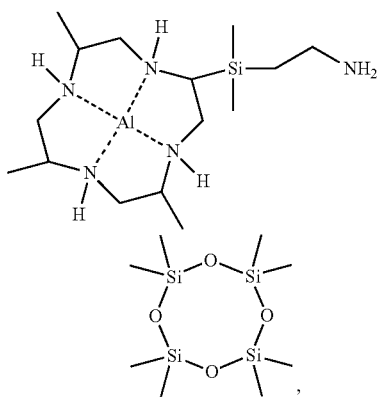

where the compound is formed by anionic ring opening polymerization of the siloxane cyclic monomer as described herein. The procedure can also be modified by replacing PAEDACE with AAEDACE.

Example 9

Preparation of Thermal Conductive Polypropylene Based on (PAEDACE)

100 g of (PAEDACE) and (AAEDACE) prepared in according to Examples 1 and 3, respectively, are transferred to a 50% master batch implementing high melt flow rate polypropylene or polyethylene and extruder. Commercial polypropylene pellets are mixed with 10% thermal conductive master batch based on PAEDACE and extruded to produce electronic cartridges. Similar cartridges are produced from commercial poly propylene and evaluated for comparison.

Example 10

Preparation of Thermal Conductive Polypropylene Based on (MAEDACE)

100 g of (MAEDACE), prepared according to Example 2, are transferred to 50% master batch implementing high melt flow rate polypropylene. Polypropylene pellets were mixed the (MAEDACE) master batch by 10% and 0.05% benzoyl peroxide and extruded to the final objects using reactive extruder. The produced electronic cartridges contain grafted (MAEDACE) on the polypropylene chains having the following chemical structure are evaluated and compared with commercial polypropylene:

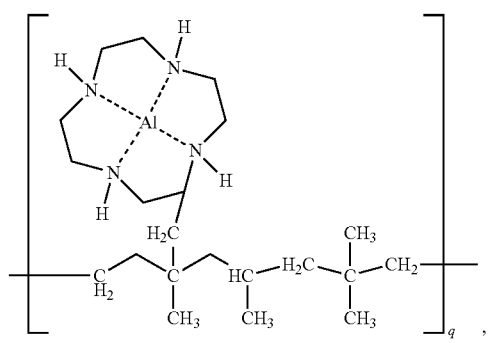

wherein q is about 100 to about 10000.

These examples demonstrate that the compositions and materials described herein can provide for superior thermal sinks with better properties than what are currently available. The superior properties could not have been predicted.

What is claimed is:

1. A thermal conductive composition comprising at least one of a compound of Formula (I):

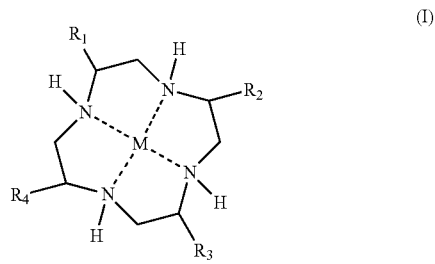

wherein:
M is Al, Ga, Si, Ge, In, or Sn;
$R_1$, $R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH—CN$, —OCN, —$CH_2OH$, $CH_2X$, $CH_2OCN$, —$CH(=O)$, provided that $R_1$, $R_2$, $R_3$, and $R_4$ are not all H,
wherein:
X is halo;
$R_5$ is $C_1$-$C_6$ alkyl;
and a compound of Formula (II):

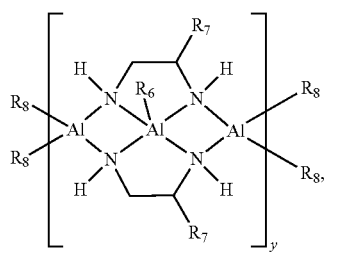

(II)

wherein:
y is about 10 to about 500;
$R_6$ is $C_1$-$C_6$ alkyl or halo;
each $R_7$ is independently —H, or —$NH_2$, —$Si(OR_9)_3$, —$Si(OR_9)_2CH_2CH_2NH_2$, —$Si(R_9)_2CH_2CH_2NH_2$, —$N^+(CH_3)_3^-OH$, —$CH_2CH(O)CH_2$, —$Si(R_9)_2CH_2CH(O)CH_2$, —$CH_3$, —$CH=CH_2$, —$CH_2CH=CH_2$, —$CH=CH—CN$, —OCN, —$CH_2OH$, $CH_2X$, $CH_2OCN$, or —$CH(=O)$, provided that each $R_7$ are not both H;
$R_8$ is —$NH—CH_2—CH_2—NH_2$ or $Al(R_{10})_2$;
$R_9$ is $C_1$-$C_6$ alkyl; and
$R_{10}$ is $C_1$-$C_6$ alkyl or halo.

2. The thermal conductive composition of claim 1, wherein $R_1$, $R_2$, $R_3$, and $R_4$ are each independently H, or $NH_2$, —$Si(OR_5)2CH_2CH_2NH_2$, $Si(OR_5)_3$, $N(CH_3)_3OH$, $CH_2CH(O)CH_2$, —$CH_3$, —$CH=CH_2$, —$CH_2CH=CH_2$, —$CH_2CH(O)CH_2$, —$CH=CH—CN$, —OCN, —$CH_2OH$, $CH_2Cl$, $CH_2OCN$, or —$CH(=O)$.

3. The thermal conductive composition of claim 1, wherein $R_7$ is H, or $NH_2$, —$Si(OR_9)_2CH_2CH_2NH_2$, $Si(OR_9)_3$, —$N^+(CH_3)_3^-OH$, $CH_2CH(O)CH_2$, —$CH_3$, —$CH=CH_2$, —$CH_2CH=CH_2$, —$CH_2CH(O)CH_2$, —$CH=CH—CN$, —OCN, —$CH_2OH$, $CH_2Cl$, $CH_2OCN$, or —$CH(=O)$.

4. The thermal conductive composition of claim 1, wherein the composition is a siloxane polymer cross linked or cured with a compound of Formula (I) or (II).

5. The thermal conductive composition of claim 4, wherein the siloxane polymer cured or cross linked with a compound of Formula (I) or (II) has a formula of:

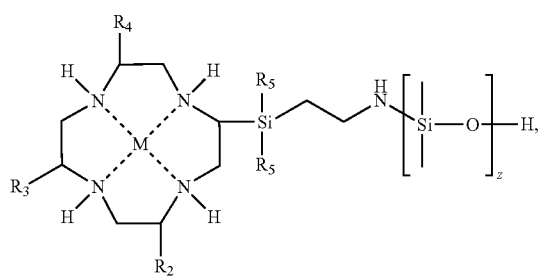

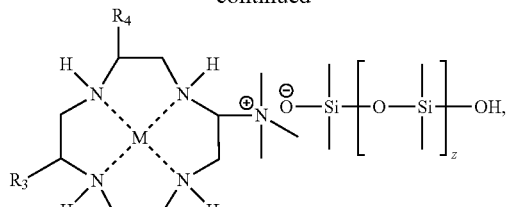

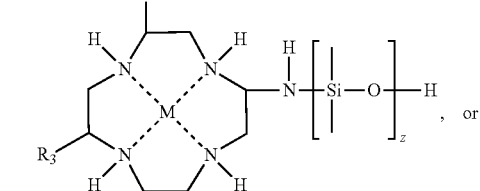

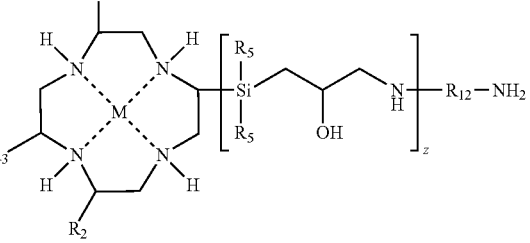

wherein
each $R_{12}$ is alkenyl, alkenylaryl, aryl or alicyclic; and
each z is independently about 1 to about 100.

6. The thermal conductive composition of claim 1, wherein the composition is a polyurethane cross linked with a compound of Formula (I) or (II).

7. The thermal conductive composition of claim 6, wherein the polyurethane cross linked with a compound of Formula (I) or (II) is a compound of Formula (III):

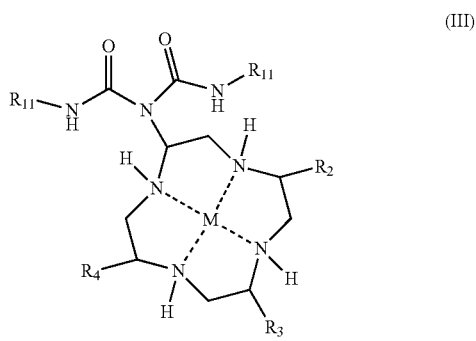

(III)

wherein:
M is Al, Ga, Si, Ge, In, or Sn;
$R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH—CN$, —OCN, —$CH_2OH$, $CH_2X$, $CH_2OCN$, —$CH(=O)$;

wherein:

X is halo;

$R_5$ is $C_1$-$C_6$ alkyl; and $R_{11}$ is a polyurethane chain.

8. The thermal conductive composition of claim 1, wherein the composition is a polyolefin copolymerized or grafted with a compound of Formula (I) or (II).

9. The thermal conductive composition of claim 8, wherein the composition has a formula of:

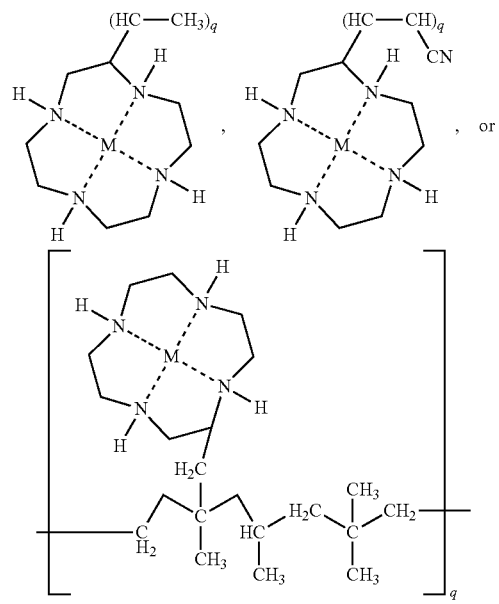

wherein

M is Al, Ga, Si, Ge, In, or Sn; and q is about 100 to about 10000.

10. A heat sink comprising at least one of a compound of Formula (I)

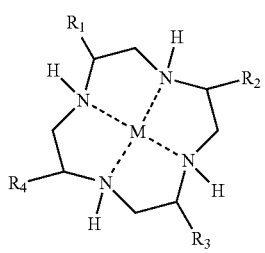

wherein:

M is Al, Ga, Si, Ge, In, or Sn;

$R_1$, $R_2$, $R_3$, and $R_4$ are each independently —H, or —$NH_2$, —Si(O$R_5$)$_3$, —Si(O$R_5$)$_2$CH$_2$CH$_2$NH$_2$, —Si($R_5$)$_2$CH$_2$CH$_2$NH$_2$, —N$^+$(CH$_3$)$_3$$^-$OH, —CH$_2$CH(O)CH$_2$, —Si($R_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H, wherein:

X is halo;

$R_5$ is $C_1$-$C_6$ alkyl;

and a compound of Formula (II):

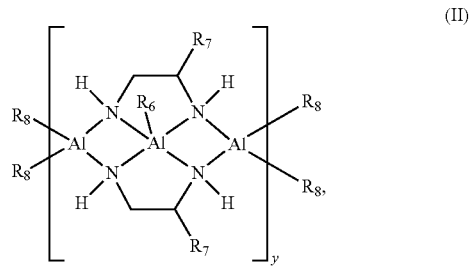

wherein:

y is about 10 to about 500;

$R_6$ is $C_1$-$C_6$ alkyl or halo;

each $R_7$ is independently —H, or —NH$_2$, —Si(O$R_9$)$_3$, —Si(O$R_9$)$_2$CH$_2$CH$_2$NH$_2$, —Si($R_9$)$_2$CH$_2$CH$_2$NH$_2$, —N$^+$(CH$_3$)$_3$$^-$OH, —CH$_2$CH(O)CH$_2$, —Si($R_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;

$R_8$ is —NH—CH$_2$—CH$_2$—NH$_2$ or Al($R_{10}$)$_2$;

$R_9$ is $C_1$-$C_6$ alkyl; and $R_{10}$ is $C_1$-$C_6$ alkyl or halo.

11. The heat sink of claim 10, wherein $R_7$ is H, —NH$_2$, —Si(O$R_9$)$_2$CH$_2$CH$_2$NH$_2$, —Si(O$R_9$)$_3$, —N$^+$(CH$_3$)$_3$$^-$OH, —CH$_2$CH(O)CH$_2$, —CH$_3$, —CH=CH$_2$, —CH$_2$CH=CH$_2$, —CH$_2$CH(O)CH$_2$, —CH=CHCN, —OCN, —CH$_2$OH, —CH$_2$Cl, —CH$_2$OCN, —CH(=O).

12. The heat sink of claim 10, wherein the composition is a siloxane polymer cured or cross linked with a compound of Formula (I) or (II).

13. The heat sink of claim 12, wherein the siloxane polymer cured or cross linked with a compound of Formula (I) or (II) a formula of:

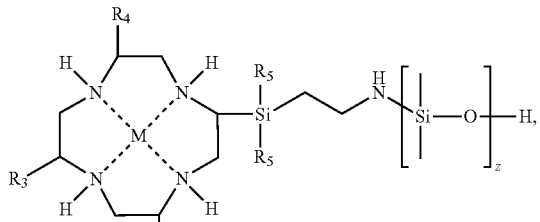

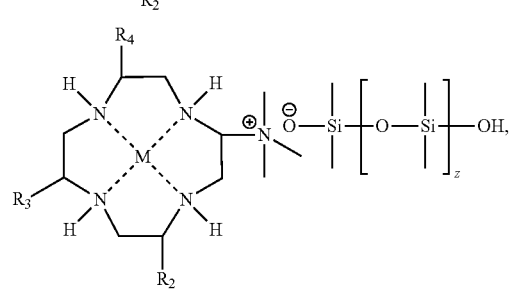

-continued

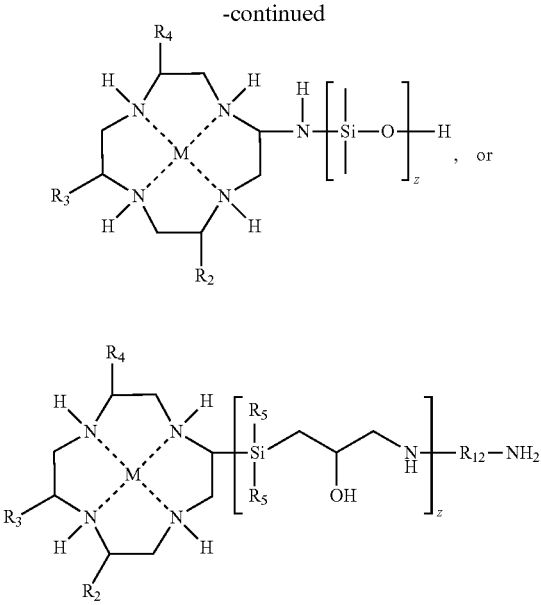

wherein
each $R_{12}$ is alkenyl, alkenylaryl, aryl or alicyclic; and
each z is independently about 10 to about 1000.

14. The heat sink of claim 10, wherein the composition is a polyurethane cross linked with a compound of Formula (I) or (II).

15. The heat sink of claim 14, wherein the polyurethane cross linked with a compound of Formula (I) or (II) is a compound of Formula (III):

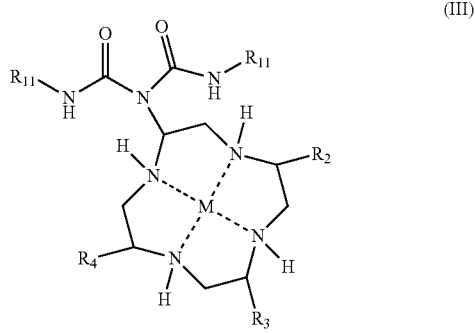

(III)

wherein:
M is Al, Ga, Si, Ge, In, or Sn;
$R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O);
wherein:
X is halo;
$R_5$ is $C_1$-$C_6$ alkyl; and
$R_{11}$ is a polyurethane chain.

16. The heat sink of claim 10, wherein the composition is a polyolefin copolymerized or grafted with a compound of Formula (I) or (II).

17. The heat sink of claim 16, wherein the polyolefin copolymerized or grafted with a compound of Formula (I) or (II) has a formula of:

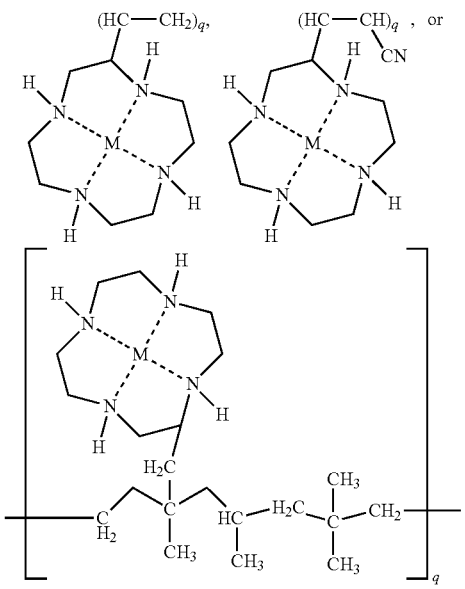

wherein
M is Al, Ga, Si, Ge, In, or Sn; and
q is about 100 to about 10000.

18. A heat transfer system or an electronic device:
the heat transfer system comprising:
at least one heat source;
at least one heat sink; and
at least one thermal conductive composition comprising at least one of a compound of Formula (I)

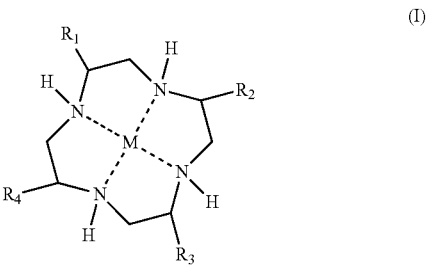

(I)

wherein:
M is Al, Ga, Si, Ge, In, or Sn;
$R_1$, $R_2$, $R_3$, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H,
wherein:
X is halo;
$R_5$ is $C_1$-$C_6$ alkyl;

or a compound of Formula (II):

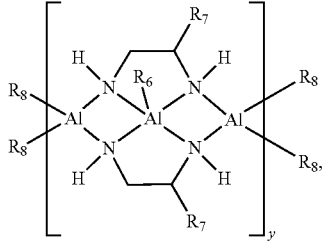

wherein:
y is about 10 to about 500;
$R_6$ is $C_1$-$C_6$ alkyl or halo;
each $R_7$ is independently —H, or —$NH_2$, —$Si(OR_9)_3$, —$Si(OR_9)_2CH_2CH_2NH_2$, —$Si(R_9)_2CH_2CH_2NH_2$, —$N^+(CH_3)_3{}^-OH$, —$CH_2CH(O)CH_2$, —$Si(R_9)_2CH_2CH(O)CH_2$, —$CH_3$, —$CH=CH_2$, —$CH_2CH=CH_2$, —$CH=CH$—$CN$, —$OCN$, —$CH_2OH$, $CH_2X$, $CH_2OCN$, or —$CH(=O)$, provided that each $R_7$ are not both H;
$R_8$ is —NH—$CH_2$—$CH_2$—$NH_2$ or $Al(R_{10})_2$;
$R_9$ is $C_1$-$C_6$ alkyl; and
$R_{10}$ is $C_1$-$C_6$ alkyl or halo;
wherein at least a portion of the thermal conductive composition is positioned substantially between the heat source and the heat sink and provides thermal communication between the heat source and heat sink; or
an electronic device, the electronic device at least partially encapsulated by a thermal conductive composition comprising at least one of a compound of Formula (I):

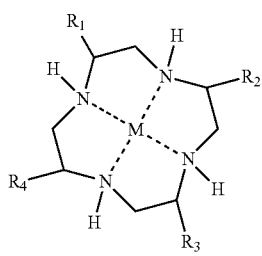

wherein:
M is Al, Ga, Si, Ge, In, or Sn;
$R_1$, $R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3{}^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH$—$CN$, —$OCN$, —$CH_2OH$, $CH_2X$, $CH_2OCN$, —$CH(=O)$, provided that $R_1$, $R_2$, $R_3$, and $R_4$ are not all H,
wherein:
X is halo;
$R_5$ is $C_1$-$C_6$ alkyl;

and a compound of Formula (II):

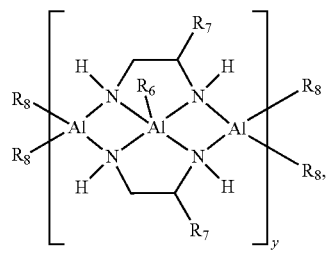

wherein:
y is about 10 to about 500;
$R_6$ is $C_1$-$C_6$ alkyl or halo;
each $R_7$ is independently —H, or —$NH_2$, —$Si(OR_9)_3$, —$Si(OR_9)_2CH_2CH_2NH_2$, —$Si(R_9)_2CH_2CH_2NH_2$, —$N^+(CH_3)_3{}^-OH$, —$CH_2CH(O)CH_2$, —$Si(R_9)_2CH_2CH(O)CH_2$, —$CH_3$, —$CH=CH_2$, —$CH_2CH=CH_2$, —$CH=CH$—$CN$, —$OCN$, —$CH_2OH$, $CH_2X$, $CH_2OCN$, or —$CH(=O)$, provided that each $R_7$ are not both H;
$R_8$ is —NH—$CH_2$—$CH_2$—$NH_2$ or $Al(R_{10})_2$;
$R_9$ is $C_1$-$C_6$ alkyl; and
$R_{10}$ is $C_1$-$C_6$ alkyl or halo.

19. A method of preparing:
a polyurethane cross-linked compound of Formula (I) or (II), the method comprising contacting a compound of Formula (I) or Formula (II)

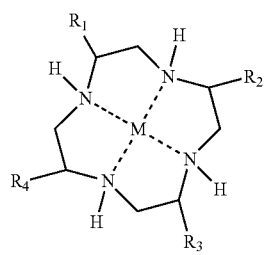

wherein:
M is Al, Ga, Si, Ge, In, or Sn;
$R_1$, $R_2$, $R_3$, and $R_4$ are each independently —H, or —$NH_2$, —$Si(OR_5)_3$, —$Si(OR_5)_2CH_2CH_2NH_2$, —$Si(R_5)_2CH_2CH_2NH_2$, —$N^+(CH_3)_3{}^-OH$, —$CH_2CH(O)CH_2$, —$Si(R_5)_2CH_2CH(O)CH_2$, —$CH_3$, —$CH=CH_2$, —$CH_2CH=CH_2$, —$CH=CH$—$CN$, —$OCN$, —$CH_2OH$, $CH_2X$, $CH_2OCN$, —$CH(=O)$, provided that $R_1$, $R_2$, $R_3$, and $R_4$ are not all H,
wherein:
X is halo;
$R_5$ is $C_1$-$C_6$ alkyl;

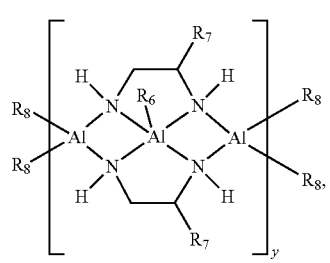

wherein:
y is about 10 to about 500;
$R_6$ is $C_1$-$C_6$ alkyl or halo;
each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with a diisocyanate and a polyol under conditions sufficient to form a polyurethane cross-linked compound of Formula (I) or (II); or,
a siloxane polymer cross linked or cured with a compound of Formula (I) or (II), the method comprising contacting a compound of Formula (I) or (II)

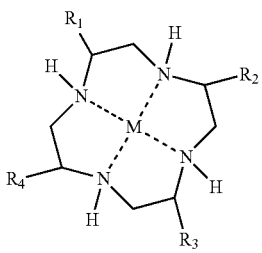

(I)

wherein:
M is Al, Ga, Si, Ge, In, or Sn;
$R_1$, $R_2$, R3, and $R_4$ are each independently —H, or —NH$_2$, —Si(OR$_5$)$_3$, —Si(OR$_5$)$_2$CH$_2$CH$_2$NH$_2$, —Si(R$_5$)$_2$CH$_2$CH$_2$NH$_2$, —N$^+$(CH$_3$)$_3$$^-$OH, —CH$_2$CH(O)CH$_2$, —Si(R$_5$)$_2$CH$_2$CH(O)CH$_2$,—CH$_3$, —CH=CH$_2$, —CH$_2$CH=CH$_2$, —CH=CH—CN, —OCN, —CH$_2$OH, CH$_2$X, CH$_2$OCN, —CH(=O), provided that $R_1$, $R_2$, $R_3$, and $R_4$ are not all H,
wherein:
X is halo;
$R_5$ is $C_1$-$C_6$ alkyl;

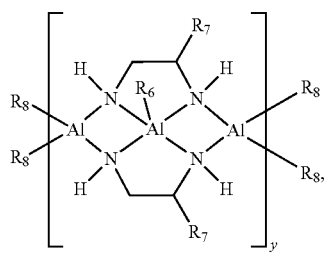

(II)

wherein:
y is about 10 to about 500;
$R_6$ is $C_1$-$C_6$ alkyl or halo;
each $R_7$ is independently —H, or —NH$_2$, —Si(OR$_9$)$_3$, —Si(OR$_9$)$_2$CH$_2$CH$_2$NH$_2$, —Si(R$_9$)$_2$CH$_2$CH$_2$NH$_2$, —N$^+$(CH$_3$)$_3$$^-$OH, —CH$_2$CH(O)CH$_2$, —Si(R$_9$)$_2$CH$_2$CH(O)CH$_2$, —CH$_3$, —CH=CH$_2$, —CH$_2$CH=CH$_2$, —CH=CH—CN, —OCN, —CH$_2$OH, CH$_2$X, CH$_2$OCN, or —CH(=O), provided that each $R_7$ are not both H;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with a siloxane cyclic monomer or silicone oil in the presence of a crosslinking agent to form the siloxane polymer cross linked or cured with a compound of Formula (I) or (II); or
polyolefin copolymerized or grafted with a compound of Formula (I) or (II), the method comprising contacting a compound of a compound of Formula (I) or (II)

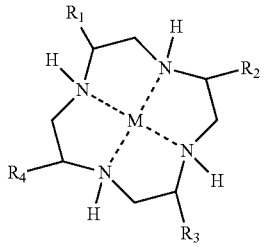

(I)

wherein:
M is Al, Ga, Si, Ge, In, or Sn;
$R_1$, $R_2$, $R_3$, and $R_4$ are each independently —CH$_2$=CH—, CH$_2$=CH CH$_2$—, or —CH$_2$=CH(CN),
wherein:
X is halo;
$R_5$ is $C_1$-$C_6$ alkyl;

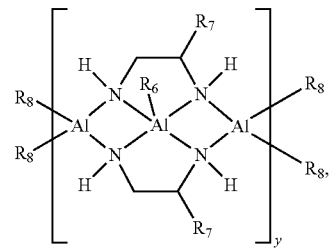

(II)

wherein:
y is about 10 to about 500;
$R_6$ is $C_1$-$C_6$ alkyl or halo;
each $R_7$ is independently CH$_2$=CH—, or CH$_2$=CHCH$_2$—, or CH$_2$=CH(CN)—;
$R_8$ is —NH—CH$_2$—CH$_2$—NH$_2$ or Al(R$_{10}$)$_2$;
$R_9$ is $C_1$-$C_6$ alkyl; and
$R_{10}$ is $C_1$-$C_6$ alkyl or halo,
with an olefin monomer under conditions suitable for free radical polymerization or anionic polymerization; or
polyolefin grafted with a compound of Formula (I) or (II), the method comprising contacting a polyolefin with a compound of Formula (I) or (II),

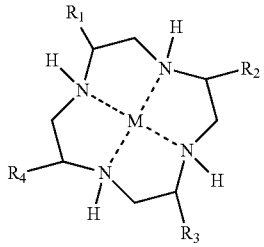

(I)

wherein:
M is Al, Ga, Si, Ge, In, or Sn;
$R_1$, $R_2$, $R_3$, and $R_4$ are —CH$_3$, wherein:
X is halo;
$R_5$ is $C_1$-$C_6$ alkyl;
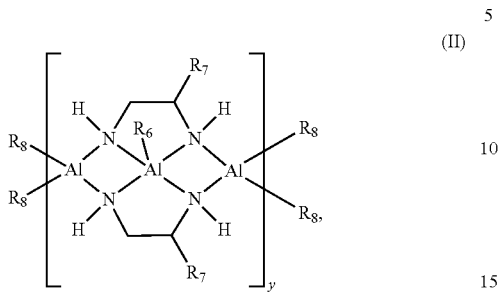
(II)
wherein:
y is about 10 to about 500;
$R_6$ is $C_1$-$C_6$ alkyl or halo;
$R_7$ is —$CH_3$;
$R_8$ is —NH—$CH_2$—$CH_2$—$NH_2$ or Al($R_{10}$)$_2$;
$R_9$ is $C_1$-$C_6$ alkyl; and
$R_{10}$ is $C_1$-$C_6$ alkyl or halo,
in the presence of a peroxide in a reactive extruder.
* * * * *

UNITED STATES PATENT AND TRADEMARK OFFICE
CERTIFICATE OF CORRECTION

PATENT NO. : 9,512,150 B2
APPLICATION NO. : 14/448938
DATED : December 6, 2016
INVENTOR(S) : Adam et al.

Page 1 of 1

It is certified that error appears in the above-identified patent and that said Letters Patent is hereby corrected as shown below:

In Column 16, Lines 20-29, delete " 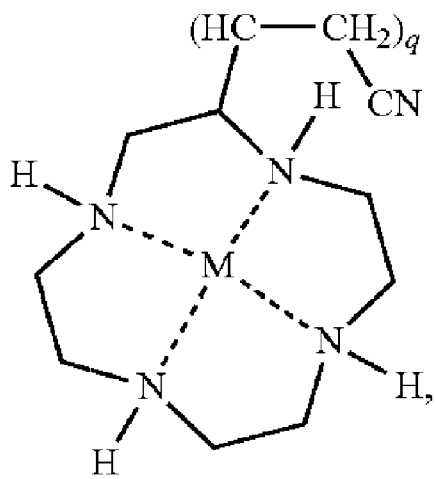 " and insert

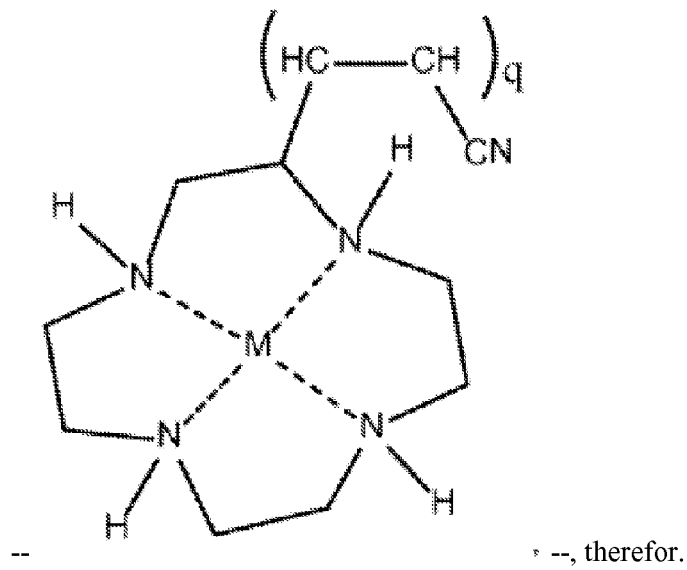

-- , therefor.

In Column 35, Line 34, in Claim 19, delete "R3," and insert -- $R_3$, -- , therefor.

Signed and Sealed this
Twenty-third Day of May, 2017

Michelle K. Lee
*Director of the United States Patent and Trademark Office*